(12) United States Patent
Villegas Escobar et al.

(10) Patent No.: US 9,839,222 B2
(45) Date of Patent: Dec. 12, 2017

(54) PROCESS FOR INCREASING BIOMASS AND SPORES PRODUCTION OF PLANT GROWTH PROMOTING BACTERIA OF THE BACILLUS GENUS

(71) Applicants: UNIVERSIDAD EAFIT, Medellin (CO); ASOCIACIÓN DE BANANEROS DE COLOMBIA (AUGURA), Medellin (CO)

(72) Inventors: Valeska Villegas Escobar, Medellín (CO); Sandra Mosquera López, Medellín (CO); Luisa Fernanda Posada Uribe, Medellín (CO); Educrecia Maria Ramírez Correa, Medellín (CO); Tatiana Zazini Cuellar Gaviria, Medellín (CO); John Jairo Mira Castillo, Medellin (CO); Luz Edith Argel Roldán, Medellin (CO)

(73) Assignees: UNIVERSIDAD EAFIT, Medellín (CO); ASOCIACION DE BANANEROS DE COLOMBIA (AUGURA), Medellín (CO)

( * ) Notice: Subject to any disclaimer, the term of this patent is extended or adjusted under 35 U.S.C. 154(b) by 130 days.

(21) Appl. No.: 14/471,345

(22) Filed: Aug. 28, 2014

(65) Prior Publication Data
US 2016/0058016 A1 Mar. 3, 2016

(51) Int. Cl.
| | |
|---|---|
| C12N 3/00 | (2006.01) |
| A01N 63/02 | (2006.01) |
| C12N 1/20 | (2006.01) |
| C12R 1/07 | (2006.01) |
| C12R 1/125 | (2006.01) |
| C12R 1/11 | (2006.01) |
| A01N 63/00 | (2006.01) |
| C05F 11/08 | (2006.01) |
| C05F 9/04 | (2006.01) |
| C05F 17/00 | (2006.01) |

(52) U.S. Cl.
CPC ............ *A01N 63/02* (2013.01); *A01N 63/00* (2013.01); *C05F 9/04* (2013.01); *C05F 11/08* (2013.01); *C05F 17/0036* (2013.01); *C12N 1/20* (2013.01); *C12N 3/00* (2013.01); *C12R 1/07* (2013.01); *C12R 1/11* (2013.01); *C12R 1/125* (2013.01); *Y02P 20/145* (2015.11); *Y02W 30/43* (2015.05)

(58) Field of Classification Search
None
See application file for complete search history.

(56) References Cited

U.S. PATENT DOCUMENTS

2010/0300166 A1 12/2010 Mena Campos et al.

FOREIGN PATENT DOCUMENTS

| WO | 2000051435 A1 | 9/2000 |
|---|---|---|
| WO | 2004024865 A2 | 3/2004 |
| WO | 2009031874 A1 | 3/2009 |
| WO | 2014178032 A1 | 11/2014 |

OTHER PUBLICATIONS

Ahimou et al., Surfactin and iturin A effects on Bacillus subtilis surface hydrophobicity, Enzyme and Microbial Technology, 27 (2000) 749-754.*
Coutte et al., Production of surfactin and fengycin by Bacillus subtilis in a bubbleless membrane bioreactor, Appl Microbiol Biotechnol, 87 (2010) 499-507.*
Villegas-Escobar et al., Fengycin C Produced by Bacillus subtilis EA-CB0015, Journal of natural Products, 76 (Mar. 5, 2013) 503-509.*
Chen et al., Greater enhancement of Bacillus subtilis spore yields in submerged cultures by optimization of medium composition through statistical experimental designs, Appl microbial Biotechnol, 85 (2010) 1353-1360.*
Jong-Hui Lim and Sang-Dal Kim, Synergistic Plant Growth Promotion by the Indigenous Auxins-producing PGPR Bacillus Subtilis AH18 and Bacillus licheniforims K11, J. Korean Soc. Appl. Biol. Chem., Jun. 5, 2009, 52(5), 531-538.
Kumar, P. et al., Bacillus strains isolated from rhizosphere showed plant growth promoting and antagonistic activity against phytopathogens, Microbiological Research, May 8, 2012, 167(2012) 493-399.
Fengyu Shi and Yingbo Zhu, Application of statistically-based experimental designs in medium optimization for spore productionof Bacillus subtilis from distillery effluent, BioControl, Jan. 20, 2007, 52:845-853.
Sayyed, R.Z., et al., Potential of Plant Growth-Promoting Rhizobacteria for Sustainable Agriculture, Bacteria in Agrobiolgy: Plant Probiotics, (2012), pp. 287-313 (D.K. Maheshwari ed., Springer-Verlag Heidelberg).
Qiao, Jun-Qing et al., Stimulation of plant growth and biocontrol by Bacillus amyloliquefaciens subsp. plantarum FZB42 engineered for improved action, Chemical and Biological Technologies in Agriculture, (2014) 1:12, pp. 1-14.
Young, Chiu-Chung, et al., Strategies for the Exploration and Development of Biofertilizer, (2012), pp. 127-139 (D. K Maheshwari ed., Springer-Verlag Heidelberg).
Amal M. Omer, Bioformulations of Bacillus Spores for using as Biofertilizer, Life Science Journal, (2010), 7(4):124-131.
Yao, A.V. et al., Effect of FZB 24 Bacillus subtilis as a biofertilizer on cotton yields in field tests, Archives of Phytopathology and Plant Protection, 2006, 39(4): 1-6.
Luisa Fernanda Posada Uribe et al., Effect of Strain Bacillus subtilis EA-CB0575 on Musa AAA Plant Growth romotion in Greenhouse, Universidad EAFIT. 2011.

* cited by examiner

*Primary Examiner* — Karen Cochrane Carlson
*Assistant Examiner* — Jennifer M. H. Tichy
(74) *Attorney, Agent, or Firm* — The Morales Law Firm, LLC; Joseph L. Morales, Esq.

(57) ABSTRACT

The present invention refers to a process designed to increase the production of plant growth-promoting microorganisms of the *Bacillus* genus, using a culture medium poor in nutrients and with specific environmental conditions, allowing to obtain a greater amount of biomass and/or spores, which can be used to prepare solid or liquid compositions to be applied to plants, aiming to promote their growth and/or counteract the effect of phytopathogenic agents.

6 Claims, 1 Drawing Sheet

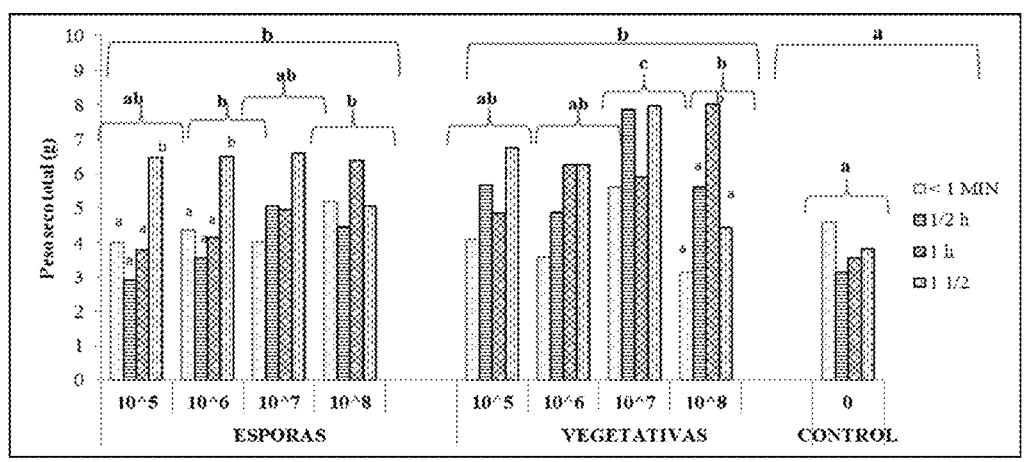
- Different letters denote significant differences (p <0.05)

PROCESS FOR INCREASING BIOMASS AND SPORES PRODUCTION OF PLANT GROWTH PROMOTING BACTERIA OF THE BACILLUS GENUS

FIELD OF THE INVENTION

The invention refers to a process for increasing the production of biomass and spores of plant growth promoting bacteria of the *Bacillus* genus. The process comprises incubating the microorganism in a suitable culture medium and cultivating it under specific physicochemical conditions, which generates a significant increase in biomass production, using less time, and with high sporulation efficiency.

DESCRIPTION OF PRIOR ART

Environmental damage caused by the use of nitrogen fertilizers, as well as the demand for environmentally safe measures by control agencies, have encouraged the search for sustainable management strategies that reduce the environmental impact of agricultural activities. An option to solve this problem is the use of plant growth-promoting microorganisms, which has proven to be effective in various plant systems (1-6).

Plant growth-promoting rhizobacteria (PGPR), including that of the *Bacillus* genus, colonize the rhizosphere of plants and have the ability to promote plant growth, either through direct mechanisms such as soil nutrient solubilization and production of phytohormones, or by indirect mechanisms such as enzyme production, nutrient competition, and generation of systemic resistance. These microorganisms can be produced rapidly in culture media and can be stored for long periods of time given they produce spores (7-10).

Various strains of some species of *Bacillus* (e.g., *B. subtilis, B. amyloliquefacines, B. cereus, B. mycoides, B. anthracis* and *B. thurigiensis*) have been identified as plant growth promoters and useful in agricultural activities (11-16). However, the definition of PGPR is made at the strain level, not at the species level. There are some publications that describe processes for the production of different growth promoting strains of the *Bacillus* genus.

WO2009031874, WO2004024865, and WO20050118011 disclose the use of various strains of *Bacillus* sp. to promote plant growth. US20030228679 describes compositions and methods to increase plant growth through inoculation with plant growth-promoting bacteria of the *B. subtilis* and *B. thuringiensis* species. CN101381692 describes a culture medium to produce PGPR made of complex nutrient sources such as molasses syrup and fermented corn juice.

Although several processes to produce *Bacillus* genus have been reported, these pose some issues due to the small amount of biomass obtained or low sporulation efficiency, which generally does not exceed 50%. Similarly, various production methods that involve improved culture media to increase the production of *Bacillus* sp. spores have been published, but the results are still very poor in terms of sporulation efficiency (17-23).

BRIEF DESCRIPTION OF THE INVENTION

The present invention refers to a process that allows increasing the production of biomass and spores from microorganisms of the *Bacillus* genus with high sporulation efficiency (over 85%), employing a suitable culture medium (SBM medium) and specific physicochemical conditions of aeration, stirring, pH, and temperature. The process of the invention reduces manipulation during the production process and increases biomass production and sporulation efficiency, which makes it much more appropriate and affordable for large scale production of the microorganism.

BRIEF DESCRIPTION OF THE FIGURE

FIG. 1 Total dry weight of banana plants inoculated with spores and vegetative cells of *Bacillus subtilis* EA-CB0575 at different microorganism concentrations and inoculation times.

DETAILED DESCRIPTION OF THE INVENTION

The process of the present invention involves, as an initial step, the activation of a microorganism of the *Bacillus* genus by cultivating it in an enriched solid culture medium (TSA), inoculating a preinoculum in a suitable culture medium, and incubating using specific physicochemical conditions in order to obtain biomass and/or spores.

In a preferred embodiment of the invention, the microorganism of the *Bacillus* genus is selected from the group consisting of *Bacillus amyloliquefaciens* EA-CB0158, *Bacillus pumilus* EA-CB0177, *Bacillus amyloliquefaciens* EA-CB0123, *Bacillus subtilis* EA-CB0575, *Bacillus altitudinis* EA-CB0686, *Bacillus megaterium* EA-CB0784, *Bacillus pumilus* 1077 and *Bacillus subtilis* EA-CB1121.

The culture medium suitable to produce PGPR microorganisms according to the invention (hereinafter SBM medium) consists of one or more carbon sources, one or more nitrogen sources, salts, macronutrients, micronutrients, pH buffers, and antifoaming agents. To prepare the SBM culture medium, the carbon source, the nitrogen source, and the macronutrients are mixed in distilled water, the resulting mixture is sterilized; once sterilized, previously sterilized aqueous solutions (stock) containing salts at concentrations between 0.1 and 1.0 molar are added.

In a preferred embodiment of the invention, the SMB medium includes one or more components selected from the group consisting of glucose, yeast extract or meat extract, $MgSO_4$, $MnCl_2$, $KH_2PO_4$, peptone, $CaCl_2$, $ZnSO_4$, NaCl, and $FeSO_4$ in a solid, semisolid or liquid matrix.

In an even more preferred embodiment of the invention, the SBM culture medium contains 1.04 g/L glucose, 0.6 g/L magnesium sulfate heptahydrate, 5.0 g/L yeast extract or meat extract, 6.0 g/L $K_2HPO_4$, 3.0 g/L peptone, 0.01 g/L NaCl, and a stock of salts consisting of 1.14 mL/L $FeSO_4*7H_2O$, 0.1M, 300 µL/L $ZnSO_4*7H_2O$ 0.1M, 9.9 mL/L $CaCl_2$ 0.1M, and 30.0 mL/L $MnCl_2$ 0.1M.

The process of the invention can be performed either in a flask or in a bioreactor. Physicochemical conditions necessary to carry out the process of the invention include temperature, pH, aeration, fermentation and stirring time. Temperature must be maintain between 25° C. and 37° C., pH must be between 5.0 and 7.5, aeration must be between 8 and 16 L/min, fermentation time must be between 48 and 72 hours, and continuous stirring must be between 300 and 600 rpm. pH can be adjusted by adding strong acids or strong bases such as $H_2SO_4$ and NaOH, while antifoaming agents, preferably of the silicone type, can be added to control foaming.

In a preferred embodiment of the invention, the process is carried out using the SBM culture medium in a 14 L bioreactor, maintaining a temperature of 30° C. for 60 hours with a pH of at least 5.5, aeration of 1.5 vvm, and continuous stirring at 430 rpm. The culture medium and the above conditions allow maximizing production of biomass and spores from microorganism *Bacillus* genus, yielding an amount of up to $1 \times 10^{10}$ CFU/mL, with sporulation efficiency greater than 92%. Centrifugation, microfiltration, decantation or thermal shock may be used to recover spores and/or biomass.

Once the microorganism has been obtained, either in the form of spores or vegetative cells, solid formulations or liquid compositions can be prepared together with one or more adjuvants and/or acceptable carriers, corresponding to another embodiment of the present invention. To prepare pesta, nor talc-based solid formulations, previously sterilized solid components are mixed with a suspension containing the microorganism and then dried at a temperature not exceeding 60° C., whereas for liquid formulations, the vegetative cells or spores of the microorganism are suspended in sterile water or other solvent and subsequently homogenized.

Preferred embodiments of the invention include talc-based formulations comprising between 5.0% and 25.0% (w/v) bacterial suspension of *B. subtillis*, between 70.0% and 99.0% (w/v) industrial talc, between 0.05% and 2.0% (w/v) carboxymethyl cellulose (CMC), and between 1.0% and 30.0% (w/v) $CaCO_3$. Similarly, other embodiments involve pesta-based formulations comprising between 5.0% and 25.0% (w/v) bacterial suspension of *B. subtillis*, between 50.0% and 75.0% (w/v) flour or semolina flour, between 1.0% and 15.0% (w/v) xanthan gum, and between 2.0% and 20.0% (w/v) industrial kaolin.

Formulations of the invention can be applied either around the stem of the plant or directly into the soil. The formulation to be applied in greenhouse can be obtained by dissolving the solid or liquid formulation in water at a ratio between 1:1 and 1:100000 based on the microorganism, yielding suspensions between $1 \times 10^5$ and $1 \times 10^{10}$ CFU/mL, which may be applied in amounts between 0.001 and 5.0 L/ha. If the formulation is to be applied in field, its volume and/or concentration must be adjusted so that a greater colonization of the microorganism is achieved as plants will be full grown and there may be more competition with microorganisms in the soil.

The growth promoting activity of the microorganism can also be assessed in vitro or in vivo, either in greenhouse or in field, in various types of crops such as bananas, corn, tomato, and *chrysanthemum*, among others. In order to establish the in vitro activity, different biochemical tests can be performed to quantify the production of metabolites (hormones, antibiotics, or siderophores) and determine the ability of phosphate solubilization and nitrogen fixation. Various inhibition assays against phytopathogenic microorganisms such as *Fusarium oxysporum, Fusarium solani, Ralstonia solanacearum* and *Mycosphaerella fijiensis*, among others, can also be carried out using enriched culture media. These assays can be performed in Petri dishes or microplates of PGRP co-cultures with phytopathogenic agents, aiming to identify growth inhibition of the harmful microorganism when exposed to PGPR.

The following examples further illustrate the invention, but it is understood that the invented concept is not limited thereto.

EXAMPLES

Example 1. Obtaining and Identifying Strains of Plant Growth Promoting Microorganisms of the *Bacillus* Genus Strains of *Bacillus* sp. were isolated from the rhizosphere of plantain plants (*Musa* AAA) originating from *Urabá* (*Antioquia*), Colombia. Rhizosphere soil and plant roots from production fields were used for this isolation process. A suspension of the samples was prepared in a phosphate buffer and subsequent serial dilutions were plated on TSA (trypticase soy agar) culture medium.

To select the *Bacillus* microorganisms, the samples were subjected to thermal shock at 80° C. for 20 minutes and resistant organisms were purified and stored in TSB medium with 20% glycerol at −80° C. (24). Table 1 shows the strains of PGPR microorganisms and their isolation source. The microorganisms were identified using 16s rDNA gene sequencing (24).

TABLE 1

PGPR bacteria, Isolation and Identification

| SPECIES | CODE | PLACE OF ISOLATION | ORIGINATING PLANT |
|---|---|---|---|
| *Bacillus amyloliquefaciens* | EA-CB0123 | Urabá, Colombia | *Musa* AAA Grand nain |
| *Bacillus amyloliquefaciens* | EA-CB0158 | Urabá, Colombia | *Musa* AAA Plantain |
| *Bacillus pumilus* | EA-CB0177 | Urabá, Colombia | *Musa* AAA Valery |
| *Bacillus pumilus* | EA-CB0570 | Urabá, Colombia | *Musa* AAA Valery |
| *Bacillus subtilis* | EA-CB0575 | Urabá, Colombia | *Musa* AAA cv. Valery |
| *Bacillus altitudinis* | EA-CB0686 | Urabá, Colombia | *Musa* AAA Grand nain |
| *Bacillus megaterium* | EA-CB0784 | Urabá, Colombia | *Musa* AAA Valery |
| *Bacillus pumilus* | EA-CB1077 | Urabá, Colombia | *Musa* AAA Valery |
| *Bacillus subtilis* | EA-CB1121 | Urabá, Colombia | *Musa* AAA Grand nain |

Example 2. Designing and Optimizing the Culture Medium

After a review of relevant literature (20, 21, 25-30), the most important sources of nutrients and macronutrients for the growth of microorganisms of the *Bacillus* genus were selected, and Placket and Burman (PBD) experiments were designed in order to identify the factors that have significant effects.

Assessed factors include the sources of carbon ($C_6H_{12}O_6$), magnesium ($MgSO_4 \cdot 7H_2O$), manganese ($MnCl_2 \cdot 4H_2O$), phosphorus-potassium ($KH_2PO_4$), and nitrogen (yeast extract, meat extract, peptone, and $(NH_4)_2SO_4$), while on the other hand, variables include viable biomass concentration (CFU/mL), spores, and sporulation rate, defined as the ratio of spores to biomass. An analysis of variance (ANOVA) with a significance level of 5% was carried out. Table 2 shows concentration ranges for each analyzed factor.

TABLE 2

Plackett and Burman design for the culture medium of the invention

| Treatment | $C_6H_{12}O_6$ | $MgSO_4 \cdot 7H_2O$ | $MnCl_2 \cdot 4H_2O$ | $KH_2PO_4$ | Yeast extract | Meat extract | Peptone | $(NH_4)_2SO_4$ |
|---|---|---|---|---|---|---|---|---|
| 1 | 2 | 0 | 0 | 6 | 5 | 5 | 0 | 4 |
| 2 | 2 | 0 | 0.5 | 6 | 5 | 0 | 3 | 4 |
| 3 | 20 | 0 | 0.5 | 0 | 0 | 0 | 3 | 4 |
| 4 | 2 | 0.5 | 0.5 | 0 | 5 | 0 | 0 | 0 |
| 5 | 20 | 0 | 0 | 0 | 5 | 5 | 3 | 0 |
| 6 | 11 | 0.3 | 0.3 | 3 | 2.5 | 2.5 | 1.5 | 2 |
| 7 | 20 | 0.5 | 0 | 6 | 5 | 0 | 3 | 0 |
| 8 | 11 | 0.3 | 0.3 | 3 | 2.5 | 2.5 | 1.5 | 2 |
| 9 | 20 | 0.5 | 0.5 | 0 | 5 | 5 | 0 | 4 |
| 10 | 11 | 0.3 | 0.3 | 3 | 2.5 | 2.5 | 1.5 | 2 |
| 11 | 2 | 0.3 | 0.5 | 6 | 0 | 5 | 3 | 0 |
| 12 | 2 | 0 | 0 | 0 | 0 | 0 | 0 | 0 |
| 13 | 20 | 0.5 | 0 | 6 | 0 | 0 | 0 | 4 |
| 14 | 20 | 0 | 0.5 | 6 | 0 | 5 | 0 | 0 |
| 15 | 2 | 0.5 | 0 | 0 | 0 | 5 | 3 | 4 |
| PB value | 0.57 | 0.041 | 0.3 | 0.6 | 0.08 | 0.02 | 0.95 | 0.21 |
| PE value | 0.01 | 0.08 | 0.99 | 0.99 | 0.99 | 0.96 | 0.98 | 0.95 |

| | FACTORS (g/L) | | | | RESPONSE VARIABLES | | |
|---|---|---|---|---|---|---|---|
| Treatment | $CaCl_2$ | $ZnSO_4 \cdot 7H_2O$ | NaCl | $FeSO_4 \cdot 7H_2O$ | Biomass (B) ($\times 10^9$ CFU/mL) | Spores (E) ($\times 10^9$ CFU/mL) | Sporulation (%) |
| 1 | 0.1 | 0.01 | 0.01 | 0.03 | 1.1 ± 1.2 | 0.6 ± 0.3 | 54.2 ± 22.0 |
| 2 | | | | | 0.0 ± 0.0 | 0 | 0.00 |
| 3 | | | | | 0.09 ± 0.0 | 0 | 0.00 |
| 4 | | | | | 0.8 ± 0.2 | 0.5 ± 0.2 | 65.5 ± 13.6 |
| 5 | | | | | 1.6 ± 1.1 | 0 | 0.0 |
| 6 | | | | | 0.4 ± 0.1 | 0 | 0.0 |
| 7 | | | | | 0.1 ± 0.0 | 0 | 0.0 |
| 8 | | | | | 0.2 ± 0.0 | 0 | 0.0 |
| 9 | | | | | 1.1 ± 0.0 | 0 | 0.0 |
| 10 | | | | | 0.1 ± 0.0 | 0 | 0.0 |
| 11 | | | | | 2.0 ± 0.0 | 1.9 ± 0.05 | 93.2 ± 0.3 |
| 12 | | | | | 0.0 ± 0.0 | 0 | 0.00 |
| 13 | | | | | 0.08 ± 0.0 | 0 | 0.00 |
| 14 | | | | | 0.06 ± 0.0 | 0 | 0.00 |
| 15 | | | | | 1.03 ± 0.0 | 0.5 ± 0.2 | 50.7 ± 16.0 |
| PE value | | | | | analysis using a significance level of α = 0.05 | | |
| PE value | | | | | | | |

Treatment No. 11 showed the best result in terms of the culture medium, using *B. subtilis* EA-CB0575 as PGPR for this specific case. It was determined that $MgSO_4 \cdot 7H_2O$ and meat extract are significant factors for the variable total biomass response, while glucose is a significant factor for spore production. The highest spore production reached at this stage of medium design was $1.1 \times 10^9$ CFU/mL, with a sporulation rate of 93%. In order to establish the most key components, individual optimization of each response variable and multivariable optimization was performed using first a full factorial design and then a central composite design. The first design significantly improved production, yielding $1.6 \times 10^8$ CFU/mL with a sporulation rate of 95%, whereas the second design yielded $1.4 \times 10^9$ CFU/mL with a sporulation rate of 94%.

In this case, the joint maximization of variables determined that a culture medium with concentrations between 1.0 and 3.0 g/L glucose; between 0.3 and 0.6 g/L $MgSO_4 \cdot 7H_2O$; between 5.0 and 10.0 g/L yeast extract or meat extract; between 4.0 and 6.0 g/L $K_2HPO_4$; between 2.0 and 5.0 g/L peptone; between 0.01 g/L NaCl, and a stock of salts composed of 1.14 mL/L $FeSO_4 \cdot 7H_2O$, 0.1M, 300 µL/L $ZnSO_4 \cdot 7H_2O$ 0.1M, 9.9 mL/L $CaCl_2$ 0.1M and 30.0 mL/L $MnCl_2$ 0.1M maximizes spore production and sporulation rate.

Example 3. Production of Biomass and Spores from *Bacillus* Genus in a Bioreactor The preinoculum was prepared by transferring three colonies of a solid culture of *B. subtilis* to 250 mL of SBM culture media. Stirring at 150 rpm was carried out for 24 hours at 30° C. The $DO_{600}$ of the preinoculum was adjusted to 2.0 with SBM sterile medium. The preinoculum was added at a ratio of 1 to 10% v/v.

An inoculum containing between $1 \times 10^5$ and $1 \times 10^9$ CFU/mL of the *Bacillus* sp. microorganism was added to 7 liters of SMB culture medium held in a BioFlo® 110 bioreactor (New Brunswick Scientific Co.) with a ring diffuser, two turbine impellers, and devices for measuring temperature, pH, and dissolved oxygen.

To ensure the required physicochemical conditions, pH was adjusted to 5.5 and temperature was maintained at 30° C. for 60 hours, with 1.5 vvm aeration, and stirring at 430 rpm. Biomass production was between $1.0 \times 10^8$ CFU/mL and $1.0 \times 10^{10}$ CFU/mL, with sporulation percentages greater than 92%. Table 3 shows each of the produced strains and the corresponding sporulation efficiency.

TABLE 3

Sporulation percentages of *Bacillus* sp. using SBM medium

| STRAIN | SPORULATION (%) |
|---|---|
| B. pumilus EA-CB0177 | 99.0 |
| B. subtilis EA-CB0575 | 92.0-95.0 |
| B. megaterium EA-CB0784 | 82.8 |
| B. subtilis EA-CB1121 | 87.4 |
| B. amyloliquefaciens EA-CB0158 | 92.7 |

Example 4. Assessing the Effect of pH

The effect of pH on growth parameters of the *B. subtilis* strains cultured in a bioreactor using SMB culture medium was assessed using an univariate design. Results (Table 4) indicate that pH in a range between 6.5 and 7.0 even without control, does not affect the production of total biomass and/or spores.

TABLE 4

Assessment of the effect of pH on the production of *Bacillus subtilis* EA-CB0575

| TREATMENT | BIOMASS ($\times 10^9$ CFU/mL) | SPORES ($\times 10^9$ CFU/mL) | SPORU-LATION (%) |
|---|---|---|---|
| pH = 6.5 | 4.1 ± 1.1 | 3.7 ± 1.2 | 90.1 ± 3.7 |
| pH = 7.0 | 2.2 ± 0.1 | 1.9 ± 0.1 | 91.1 ± 13.1 |
| Without pH control | 2.4 ± 0.4 | 2.3 ± 0.6 | 92.9 ± 5.1 |
| P value | 0.209 | 0.285 | 0.895 |

Different letters denote significant differences ($p < 0.05$)

Example 5. Assessing the Effect of Stirring and Aeration

The effect of stirring and aeration when using a 14 L bioreactor in the process of the present invention was assessed for *B. subtilis* EA-CB0575 through a central composite design (CCD) with star points, aiming to optimize the production of biomass and spores. Biomass and spores were quantified in CFU/mL through surface plaiting and dry weight in g/L, reducing sugars at the end of fermentation were also quantified.

According to the results, stirring between 400 and 450 rpm and aeration between 10 to 12 L/min maximizes the production of spores and the sporulation percentage, obtaining values between $8.0 \times 10^9$ and $1.0 \times 10^{10}$ spores/mL and a sporulation efficiency of about 94%.

Example 6. PGPR Microorganism Formulations

Microorganisms of the *Bacillus* genus obtained according to Example 3 can be formulated either to obtain aqueous suspensions of concentrations between $1 \times 10^6$ and $1 \times 10^{11}$ CFU/mL of spores or vegetative cells, or to obtain pesta or talc-based solid formulations by incorporating adjuvants such as CMC, kaolin, xanthan gum, and calcium carbonate at concentrations between 0.5% and 25.0% (w/w).

To prepare said formulations, the adjuvants must be initially sterilized and then mixed with the microbial active principle and water in a ratio of 1:10 to 1:100 (v/v). Once mixed, they are left to dry at 60° C. for 30 minutes and, lastly, they are hermetically packaged and stored in suitable conditions.

Example 7. Applying a PGPR Microorganism to Bananas

A PGPR microorganism of *Bacillus* sp., particularly *B. subtilis* EA-CB0575, was applied to banana (*Musa* AAA) at different stages of plant growth. The plants were immersed for more than 60 minutes in aqueous suspensions of the microorganism at concentrations of $1.0 \times 10^6$, $1.0 \times 10^7$, and $1.0 \times 10^8$ CFU/mL, using spores or vegetative cells. Subsequently, the plants were cultured in peat for the corresponding hardening and rooting stages in a greenhouse at temperatures above 30° C. and relative humidity greater than 80%.

FIG. 1 shows the dry weight of plants four months after the application of spores and vegetative cells of *Bacillus subtilis* EA-CB0575 in a greenhouse in banana plants using various inoculation times and concentrations of the microorganism.

Results show that there is a significant increase (from 11% to 120%) in the total dry weight when banana plant roots are inoculated with spores or vegetative cells of *Bacillus*. Best inoculation times are those over half an hour and at concentrations greater than $1 \times 10^6$ CFU/mL of spores or vegetative cells.

Additionally, an assay in greenhouse and in field was conducted to assess other growth promoting microorganisms of the *Bacillus* genus (*B. megaterium* and *B. cereus*) in banana plants (*Musa* AAA). Table 5 shows formulation applied, strained used, and fruit production time, which decreased up to 1.5 months in relation the absolute control.

TABLE 5

Formulations assessed in greenhouse and field in banana (*Musa* AAA)

| COMPOSITION | STRAIN USED | TIME (months) |
|---|---|---|
| PESTA 0 | No microorganism | 7.4 cd |
| TALC 0 | No microorganism | 7.5 cd |
| Pesta No. 1 | EA-CB0131 (*B. cereus*) | 7.1 abc |
| Talc No. 1 | EA-CB0131 (*B. cereus*) | 7.1 abc |
| Pesta No. 2 | EA-CB0784 (*B. megaterium*) | 7.6 de |
| Talc No. 2 | EA-CB0784 (*B. megaterium*) | 7.3 abcd |
| Pesta No. 3 | EA-CB0575 (*B. subtilis*) | 6.7 a |
| Talc No. 3 | EA-CB0575 (*B. subtilis*) | 7.3 abc |
| Pesta No. 4 | EA-CB1121 (*B. subtilis*) | 7.3 bcd |
| Talc No. 4 | EA-CB1121 (*B. subtilis*) | 6.9 ab |
| ABSOLUTE CONTROL | No microorganism | 8.3 e |

Different letters denote significant differences ($p < 0.05$)

Example 8. Assessing Growth Promoting Activity of PGPR in Other Crops

Growth promoting activity of PGPR microorganisms of the *Bacillus* genus was assessed in corn, coriander, and tomato plants using vegetative cells. This assessment was performed by inoculating the microorganism into seeds, and then into the substrate of the seedlings that germinated after the first inoculation, at a concentration of $1 \times 10^8$ CFU/mL. Table 6 shows the results of the strains assessed in the aforementioned crops.

TABLE 6

Growth promotion of various *Bacillus* genus PGPR

| | Total dry weight (g) | | |
|---|---|---|---|
| Microorganism | Corn | Coriander | Tomato |
| B. cereus EA-CB0131 | N/D | 22.5 bc | N/D |
| B. amyloliquefaciens EA-CB0158 | 6.6 bc | 21.0 ab | 0.04 c |
| B. pumilus EA-CB0177 | 5.6 ab | 22.6 bc | 0.04 c |
| B. pumilus EA-CB0570 | N/D | N/D | 0.03 ab |
| B. subtilis EA-CB0575 | 7.5 cd | 24.0 c | 0.04 bc |
| B. altitudinis EA-CB0686 | 5.6 ab | 24.3 c | 0.04 c |
| B. megaterium EA-CB0784 | 6.2 abc | N/D | 0.04 c |
| B. pumilus EA-CB1077 | 6.2 abc | N/D | N/D |
| B. subtilis EA-CB01121 | 8.3 d | 24.4 c | 0.04 bc |
| ABSOLUTE CONTROL | 5.0 a | 19.5 a | 0.02 a |
| P value | 0.003 | 0.002 | 0.008 |

Different letters denote significant differences ($p < 0.05$)

According to the results, total dry plant weight significantly increased in corn between 10.5% and 65.5%; in cilantro between 7.6% and 25.7%; and in tomato between 50.0% 100% in relation to the control without inoculation after growing for 3 weeks in a greenhouse.

To determine the in vitro growth promoting potential of various *Bacillus* sp., production of siderophores, auxins, phosphate solubilization, nitrogen fixation, and phytopathogenic antagonism capacity were assessed in vitro. Biochemical tests carried out in vitro determined the presence or absence of PGPR characteristics in the assessed isolates. The and PGPR biochemical traits of the *Bacillus* sp. strains, showing that *B. subtillis* EA-CB0575 and EA-CB0158 have the highest potential.

Example 9. Assessing Antagonism and PGPR Biochemical Traits for *Bacillus* Genus To determine the in vitro growth promoting potential of various *Bacillus* genus, production of siderophores, auxins, phosphate solubilization, nitrogen fixation, and phytopathogenic antagonism capacity were assessed in vitro. Biochemical tests carried out in vitro determined the presence or absence of PGPR characteristics in the assessed isolates. The Salkowsky colorimetric method (31) was used to assess auxin production; the CAS colorimetric method (32) was used to assess siderophore production; the protocol reported by Parson y Strickland 1972 (33) was used to determine phosphate solubilization; and the studied strain was cultured in nitrogen-free Nfb medium (34) to assess nitrogen fixation.

Co-cultures of PGPR and phytopathogenic agents *Fusarium oxysporum* EAP004, *Fusarium solani* EAP-005, *Botritys cinerea* EAP-001, *Mycosphaerella fijiensis*, and *Ralstonia solanacearum* EAP-009 were performed to assess phytopathogenic antagonism using PDA culture medium; except for *Ralstonia solanacearum*, where BGTA culture medium was used. Table 7 illustrates the antagonism results and PGPR biochemical traits of the *Bacillus* sp. strains, showing that *B. subtillis* EA-CB0575 and EA-CB0158 have the highest potential.

TABLE 7

PGPR traits and phytopathogenic antagonism by *Bacillus* genus.

| | Antagonism | | | | | PGPR biochemical traits | | | |
|---|---|---|---|---|---|---|---|---|---|
| MICROORGANISM | F. oxysporum | F. solani | B. cinerea | M. fijiensis | R. solanacearum | AIA (ug/mL) | Siderophores (mM) | Phosphate solubilization | Nitrogen fixation (Nfb) |
| B. amyloliquefaciens EA-CB0123 | ++ | n/d | n/d | ++ | +++ | 2 | 0 | – | – |
| B. amyloliquefaciens EA-CB0158 | +++ | +++ | ++ | – | ++ | 14 | 4 | – | – |
| B. pumilus EA-CB0177 | – | – | – | – | – | 48 | 0 | – | – |
| B. pumilus EA-CB0570 | – | – | – | – | – | 34 | 6.8 | – | + |
| B. subtilis EA-CB0575 | +++ | ++ | ++ | ++ | ++ | 9 | 16 | – | + |
| B. altitudinis EA-CB0686 | – | – | – | – | – | 11 | 3 | – | – |
| B. megaterium EA-CB0784 | – | – | – | – | – | 34 | 7 | + | + |
| B. pumilus EA-CB1077 | – | – | – | – | – | 25 | 0 | – | – |
| B. subtilis EA-CB1121 | – | – | – | – | – | 9 | 2 | – | – |

(+): Low antagonism;
(++): Average antagonism;
(+++): High antagonism.
(–): Antagonism or compound production not detected
n/d: Not determined.

Salkowsky colorimetric method (31) was used to assess auxin production; the CAS colorimetric method (32) was used to assess siderophore production; the protocol reported by Parson y Strickland 1972 (33) was used to determine phosphate solubilization; and the studied strain was cultured in nitrogen-free Nfb medium (34) to assess nitrogen fixation.

Co-cultures of PGPR and phytopathogenic agents *Fusarium oxysporum* EAP004, *Fusarium solani* EAP-005, *Botritys cinerea* EAP-001, *Mycosphaerella fijiensis*, and *Ralstonia solanacearum* EAP-009 were performed to assess phytopathogenic antagonism using PDA culture medium; except for *Ralstonia solanacearum*, where BGTA culture medium was used. Table 7 illustrates the antagonism results

REFERENCES

1. Erturk Y., Ercisli S., Haznedar A., Cakmakci R. 2010. Effects of plant growth promoting rhizobacteria (PGPR) on rooting and root growth of kiwifruit (*Actinidia deliciosa*) stem cuttings. Biological Research 43.
2. Kavino M., Harish S., Kumar N., Saravanakumar D., Samiyappan R. 2010. Effect of chitinolytic PGPR on growth, yield and physiological attributes of banana (*Musa* spp.) under field conditions. Applied Soil Ecology 45:71-77.
3. Raupach G., Kloepper J. 2000. Biocontrol of cucumber diseases in the flied by plant growth promoting rhizobacteria with and without methyl bromide fumigation. Plant disease 84:1073-1075.
4. Kumar H., Dubey R. C., Maheshwari D. K. 2011. Effect of plant growth promoting rhizobia on seed germination, growth promotion and suppression of Fusarium wilt of fenugreek (Trigonella foenum-graecum L.). Crop Protection 30:1396-1403.
5. Lim J-H., Kim S-D. 2013. Induction of Drought Stress Resistance by Multi-Functional PGPR Bacillus licheniformis K11 in Pepper. Plant Pathology Journal 29:201-208.
6. Singh J. S., Pandey V. C., Singh D. P. 2011. Efficient soil microorganisms: A new dimension for sustainable agriculture and environmental development. Agriculture Ecosystems & Environment 140:339-353.
7. Bais H. P., Fall R., Vivanco J. M. 2004. Biocontrol of Bacillus subtilis against infection of Arabidopsis roots by Pseudomonas syringae is facilitated by biofilm formation and surfactin production. Plant Physiology 134:307-319.
8. Kumar A., Prakash A., Johri B N. 2011. Bacillus as PGPR in Crop Ecosystem.
9. Ongena M., Jacques P. 2008. Bacillus lipopeptides: versatile weapons for plant disease biocontrol. Trends in Microbiology 16.
10. Szczech M., Shoda M. 2005. The influence of Bacillus subtilis RB14-C on the development of Rhizoctonia solani and indigenous microorganisms in the soil. Canadian Journal of Microbiology 51:405-411.
11. Cassán F., Sgroy V., Perrig D., Masciarelli O., Luna V. 2005. Producción de fitohormonas por Azospirillum sp. aspectos fisiológicos y tecnológicos de la promoción de crecimiento vegetal.
12. Hayat R., Ali S., Amara U., Khalid R., Ahmed I. 2010. Soil beneficial bacteria and their role in plant growth promotion: a review. Annals of Microbiology 60:579-598.
13. Kloepper J., Yan Z., Ryu C., Mc Inroy J., Reddy M. S. 2000. Effect of PGPR dosage on plant growth promotion and induced systemic resistance, p. 14. Dept. of Entomology & Plant Pathology, Auburn, USA.
14. Ramos B., Garcia J. A. L., Probanza A. N., Barrientos M. L., Gutierrez Mañero F. J. 2003. Alterations in the rhizobacterial community associated with European alder growth when inoculated with PGPR strain Bacillus licheniformis. Environmental and Experimental Botany 49:61-68.
15. Rana A., Saharan B., Joshi M., Prasanna R., Kumar K., Nain L. 2011. Identification of multi-trait PGPR isolates and evaluating their potential as inoculants for wheat. Annals of Microbiology 61:893-900.
16. Upadhyay S. K., Singh J. S., Saxena A. K., Singh D. P. 2012. Impact of PGPR inoculation on growth and antioxidant status of wheat under saline conditions. Plant Biology 14.
17. Cho J. H., Kim Y. B., Kim E. K. 2009. Optimization of culture media for Bacillus species by statistical experimental design methods. Korean Journal of Chemical Engineering 26:754-759.
18. Deepak V., Kalishwaralal K., Ramkumarpandian S., Babu S. V., Senthilkumar S. R., Sangiliyandi G. 2008. Optimization of media composition for Nattokinase production by Bacillus subtilis using response surface methodology. Bioresource Technology 99:8170-8174.
19. Donnellan J. E., Nags E. H., Levinson H. S. 1964. Chemically defined synthetic media for sporulation and for germination and growth of Bacillus subtilis. Journal of bacteriology 87:332-336.
20. Gu X-B., Zheng Z-M., Yu H-Q., Wang J., Liang F-L., Liu R-L. 2005. Optimization of medium constituents for a novel lipopeptide production by Bacillus subtilis MO-01 by a response surface method. Process Biochemistry 40:3196-3201.
21. Monteiro S. M., Clemente J. J., Henriques A. O., Gomes R. J., Carrondo M. J., Cunha A. E. 2005. A procedure for high-yield spore production by Bacillus subtilis. Biotechnology Progress 21:1026-1031.
22. Penna T. C. V., Machoshvili I. A., Ishii M. 2003. Effect of media on spore yield and thermal resistance of Bacillus stearothermophilus. Applied Biochemistry and Biotechnology 105:287-294.
23. Purohit M., Sassi-Gaha S., Rest R. F. 2010. Rapid sporulation of Bacillus anthracis in a high iron, glucose-free medium. Journal of Microbiological Methods 82:282-287.
24. Ramirez C. M. 2011. Bacterias rizosféricas formadoras de endospora en Musa spp. bajo diferentes manejos agronómicos y su potencial para promover crecimiento vegetal. Masters in Biology. Universidad de Medellín, Colombia.
25. Luna C. L, Silva G. R., Rios E. M. M. 2004. Bacillus thuringiensis var. israelensis; production involving re-use of the supernatant. Biotechnology Letters 26:143-145.
26. Prabakaran G., Balaraman K. 2006. Development of a cost-effective medium for the large scale production of Bacillus thuringiensis var israelensis. Biological Control 36:288-292.
27. Rao Y. K, Tsay K-J., Wu W-S., Tzeng Y-M. 2007. Medium optimization of carbon and nitrogen sources for the production of spores from Bacillus amyloliquefaciens B128 using response surface methodology. Process Biochemistry 42:535-541.
28. Souza C., Rodrigues R., Ayub M. 2009. Effects of oxygen volumetric mass transfer coefficient on transglutaminase production by Bacillus circulans BL32. Biotechnology and Bioprocess Engineering 14:571-576.
29. Veening J. W., Smits W. K., Hamoen L. W., Kuipers O. P. 2006. Single cell analysis of gene expression patterns of competence development and initiation of sporulation in Bacillus subtilis grown on chemically defined media. Journal of Applied Microbiology 101:531-541.
30. Zouari N., Dhouib A., Ellouz R., Jaoua S. 1998. Nutritional requirements of a strain of Bacillus thuringiensis subsp. kurstaki and use of gruel hydrolysate for the formulation of a new medium for δ-endotoxin production. Applied Biochemistry and Biotechnology 69:41-52.
31. Patten C. L., Glick B. R. 2002. Role of Pseudomonas putida indoleacetic acid in development of the host plant root system. Applied and Environmental Microbiology 68:3795-3801.
32. Schwyn B., Neilands J. B. 1987. UNIVERSAL CHEMICAL ASSAY FOR THE DETECTION AND DETERMINATION OF SIDEROPHORES. Analytical Biochemistry 160:47-56.
33. Strickland J. D. H., T. R. P. 1972. A practical handbook of seawater analysis.
34. Döbereiner J. 1988. Isolation and identification of root Associated diazotrophs. Plant and Soil 110: 207-212.

Applicant has made a deposit of the novel strains listed in this Application in the isolated Musa sp. (EA-CB) bacteria collection registered under Registration No. 191 in the Von Humboldt Institute, Calle 28A #15-09, Bogotá, Colombia, South America. Access to these novel strains will be available during the pendency of the application to the Commissioner of Patents and Trademarks and persons determined by the Commissioner to be entitled thereto upon request. Upon allowance of any claims in the application, the Applicant will make the deposit available to the public pursuant to 37 C.F.R.sctn.1.808. This deposit of *Bacillus Subtilis* strains will be maintained in the Von Humboldt depository, which is a public depository, for a period of 30 years, or 5 years after the most recent request, or for the enforceable life of the patent, whichever is longer, and will be replaced if it becomes nonviable during that period. Additionally, Applicant has or will satisfy all the requirements of 37 C.F.R. §§1.801-1.809, including providing an indication of the viability of the sample upon deposit. Applicant has no authority to waive any restrictions imposed by law on the transfer of biological material or its transportation in commerce. The strains *Bacillus subtilis* EA-CB0575, *Bacillus altitudinis* EA-CB0686, *Bacillus subtilis* EA-CB1121, *Bacillus megaterium* EA-CB0784, *Bacillus pumilus* EA-CB0177, *Bacillus amyloliquefaciens* EA-CB0158, *Bacillus amyloliquefaciens* EA-CB0123, and *Bacillus pumilus* EA-CB1077 are available to the public through the National Register of biological collections (RNC, by its acronym in Spanish), under the Registration Number 191.

It should be understood that the present invention is not limited to the embodiments described and illustrated herein. As it will be apparent to one skilled in the art, there are potential variations and modifications that do not depart from the spirit of the invention, which is only defined by the following claims:

The invention claimed is:

1. A procedure for increasing production of biomass and/or spores obtained from plant growth promoting microorganisms of the *Bacillus* genus, comprising:
    a) preparing a preinoculum by transferring one or more colonies from a culture of *Bacillus* sp. in suitable culture medium (SBM) and incubating for 10 to 24 hours at 30 to 38° C.
    b) adding 1 to 10% of the preinoculum from step a) to a suitable volume of SBM to obtain a culture;
    c) incubating the culture obtained in step b) for 10 to 20 hours at 25° C. to 38° C., stirring between 50 to 500 rpm, and aeration rates between 1 to 200 L/min;
    d) recovering biomass and/or spores of *Bacillus* sp.; wherein the SBM culture medium comprises: at least one monosaccharide selected from the group consisting of glucose and sucrose between 1.0 and 3.0 g/L; a nitrogen source selected from yeast extract or meat extract between 3.0 and 5.0 g/L; peptone between 3.0 and 5.0 g/L; $MgSO_4$; $KH_2PO_4$; NaCl; $FeSO_4$; $ZnSO_4$; $CaCl_2$; and $MnCl_2$ in a solid, semisolid or liquid matrix.

2. The procedure according to claim 1, wherein at least 85% of the biomass obtained corresponds to the spore form of the microorganism.

3. The procedure according to claim 1, wherein the microorganism is selected from the group consisting of *Bacillus subtilis* EA-CB0575, *Bacillus altitudinis* EA-CB0686, *Bacillus subtilis* EA-CB 1121, *Bacillus megaterium* EA-CB0784, *Bacillus pumilus* EA-CB0177, *Bacillus amyloliquefaciens* EA-CB0158, *Bacillus amyloliquefaciens* EA-CB0123, and *Bacillus pumilus* EA-CB 1077.

4. The procedure according to claim 1, wherein the suitable culture medium has the following composition: glucose between 1.0 and 3.0 g/L, $MgSO_4*7H_2O$ between 0.3 and 0.6 g/L, $KH_2PO_4$ between 5.0 and 10.0 g/L, yeast extract between 3.0 and 5.0 g/L, peptone between 2.0 and 5.0 g/L, 0.01 g/L of NaCl, 0.03 g/L of $FeSO_4*7H_2O$ 0.1M, 0.01 g/L of $ZnSO_4*4H_2O$ 0.1 M, 0.11 g/L of $CaCl_2$ 0.1 M, and 0.5 g/L of $MnCl_2*4H_2O$ 0.1 M.

5. The procedure according to claim 1, wherein step c) is carried out in a flask or in a bioreactor.

6. The procedure according to claim 1, wherein step d) is carried out through one or more ultrafiltration, centrifuge and thermal shock processes.

* * * * *